US008038974B2

(12) United States Patent
Deckers et al.

(10) Patent No.: US 8,038,974 B2
(45) Date of Patent: Oct. 18, 2011

(54) AQUEOUS SOLUTIONS CONTAINING METAL CYANIDE FOR CYANIDE LEACHING FOR THE WINNING OF GOLD AND SILVER

(75) Inventors: Andreas Deckers, Flomborn (DE); Thomas Schneider, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/278,222

(22) PCT Filed: Jan. 22, 2007

(86) PCT No.: PCT/EP2007/050592
§ 371 (c)(1), (2), (4) Date: Aug. 4, 2008

(87) PCT Pub. No.: WO2007/090725
PCT Pub. Date: Aug. 16, 2007

(65) Prior Publication Data
US 2009/0039315 A1 Feb. 12, 2009

(30) Foreign Application Priority Data
Feb. 3, 2006 (EP) .................................... 06101295

(51) Int. Cl.
*C01C 3/08* (2006.01)
*C01C 3/02* (2006.01)
*C01C 3/00* (2006.01)
*C01D 3/08* (2006.01)
*B01D 11/00* (2006.01)

(52) U.S. Cl. ............ 423/379; 423/27; 423/29; 423/179; 423/236; 423/372

(58) Field of Classification Search ............. 252/182.34; 423/379, 27, 29, 179, 236, 372
See application file for complete search history.

(56) References Cited

U.S. PATENT DOCUMENTS

| 3,619,132 | A | 11/1971 | Mann et al. | |
|---|---|---|---|---|
| 4,687,559 | A * | 8/1987 | Coburn et al. | ............. 205/560 |
| 4,721,526 | A | 1/1988 | Elmore et al. | |
| 4,847,062 | A | 7/1989 | Rogers et al. | |
| 5,254,153 | A | 10/1993 | Mudder | |
| 5,368,830 | A | 11/1994 | Alfano et al. | |
| 6,162,263 | A | 12/2000 | Day et al. | |
| 6,896,863 | B2 * | 5/2005 | Rogers et al. | ............. 423/379 |
| 2004/0197256 | A1 | 10/2004 | Rogers et al. | |

FOREIGN PATENT DOCUMENTS

DE 37 36 243 5/1989
DE 10 2005 026 326 12/2006

* cited by examiner

*Primary Examiner* — Ling Choi
*Assistant Examiner* — Monique Peets
(74) *Attorney, Agent, or Firm* — Oblon, Spivak, McClelland, Maier & Neustadt, L.L.P.

(57) ABSTRACT

The present invention relates to solutions comprising water and at least one metal cyanide, at least a part of the water being obtained from wastewater which occurs as depleted wastewater in a process for extracting noble metals from noble metal-containing ores by the cyanide process, the process for the preparation of solutions according to the invention and to the use of the solutions according to the invention in a process for extracting noble metals from noble metal-containing ores by the cyanide process, to a process for extracting noble metals from noble metal-containing ores by the cyanide process, wherein the solution according to the invention is used, and to the use of depleted wastewater occurring in the extraction of noble metals from noble metal-containing ores by the cyanide process to the preparation of solutions comprising water and at least one metal cyanide.

10 Claims, No Drawings

AQUEOUS SOLUTIONS CONTAINING METAL CYANIDE FOR CYANIDE LEACHING FOR THE WINNING OF GOLD AND SILVER

The present invention relates to solutions comprising water and at least one metal cyanide, at least a part of the water being obtained from wastewater which occurs as depleted wastewater in a process for extracting noble metals from noble metal-containing ores by the cyanide process, the process for the preparation of solutions according to the invention and to the use of the solutions according to the invention in a process for extracting noble metals from noble metal-containing ores by the cyanide process, to a process for extracting noble metals from noble metal-containing ores by the cyanide process, wherein the solution according to the invention is used, and to the use of depleted wastewater occurring in the extraction of noble metals from noble metal-containing ores by the cyanide process to the preparation of solutions comprising water and at least one metal cyanide.

An important field of use for aqueous cyanide-containing solutions is the cyanide process for extracting noble metals from noble metal-containing ores. The process is used in general for extracting noble metals from ores which comprise small proportions of noble metal, so that extraction of the noble metals by other processes known in the prior art is not economical.

In the cyanide process, comminuted and, if appropriate, agglomerated noble metal-containing ore is usually treated with an aqueous cyanide-containing solution in the presence of oxygen. The formation of a noble metal-cyanide complex is utilized for separating the noble metal present in the ore from other metals. This process is used in general for extracting silver and gold from silver- and gold-containing ores. The formation of a gold-cyanide complex is shown by way of example below:

The noble metal—in the present case the gold—is present in complexed form in aqueous solution after the treatment of the ore with the aqueous cyanide-containing solution in the presence of oxygen. The gold-containing solution is then generally separated from the ore residues and the gold is extracted, for example, by precipitation using zinc dust:

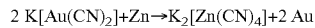

In addition to the precipitation of the gold with the aid of zinc dust, further processes for extracting gold are known in the prior art, for example adsorption with the aid of active carbon.

After the abovementioned extraction of the noble metal, in particular of the gold, by the cyanide process, a wastewater which is depleted with respect to noble metals and comprises cyanide and, if appropriate, heavy metals and further solids remains behind. The wastewater which is depleted with respect to noble metals and comprises unreacted toxic cyanide can optionally be circulated without the cyanide content being increased, and in this way is brought into contact again with noble metal-containing ore. At the end of the process for noble metal extraction by the cyanide process, however, a contaminated and cyanide-laden wastewater is obtained and generally has to be disposed of at high costs.

Suitable processes for the extraction of noble metals by means of the cyanide process are known in the prior art and are disclosed, for example, in Ullmann's Encyclopedia, 6th edition, 2000, Electronic Release, chapter on Gold, Gold Alloys and Gold Compounds, 4. Production. Special cyanide extraction processes which relate in particular to heap leaching are likewise disclosed in the prior art.

Thus, DE-A 37 36 243 relates to a process and a plant for the extraction of gold from gold ore. The process comprises the extraction of gold from gold ore by comminution, agglomeration and leaching, the ore being comminuted in one operation by application of stress in a material bed and at the same time being agglomerated. DE-A 37 36 243 provides no information with regard to a further use of the wastewater depleted with respect to gold after recovery of the gold.

U.S. Pat. No. 4,721,526 relates to a process for the heap leaching of gold and silver ores, the amount of gold and silver extractable from the ores being increased by passing in, during the cyanide extraction, a gas which has a larger amount of oxygen than air. The gold or silver is recovered from the liquor enriched in gold or silver by the zinc precipitation or adsorption of active carbon or the like. The solution depleted with respect to gold or silver can be recycled for heap leaching. Aqueous cyanide solutions wherein a part of the water is obtained from wastewater and the preparation processes thereof are not disclosed in U.S. Pat. No. 4,721,526.

U.S. Pat. No. 5,368,830 relates to a cyanide process, the formation and deposition of calcium carbonate on various metallic surfaces and active carbon or further surfaces which are present in apparatuses for the cyanide process being avoided. The avoidance is achieved by adding small amounts of polyetherpolyaminomethylene phosphonates to the aqueous solutions used for the cyanide process. According to U.S. Pat. No. 5,368,830, the depleted wastewater obtained in the cyanide process after extraction of the noble metal can be "revitalized" again by addition of cyanide and calcium chloride and used again for the cyanide process, in particular for heap leaching. Solutions comprising water and at least one metal cyanide, a part of the water being obtained from wastewater, and preparation processes therefore are not disclosed in U.S. Pat. No. 5,368,830.

The preparation of the cyanides used for the cyanide process is likewise known from the prior art and disclosed, for example, in Ullmann's Encyclopedia, 6th Edition, 2000, Electronic Release, chapter on Cyano Compounds, Inorganic. Further processes for the preparation of alkali metal cyanides, in particular sodium cyanide, are disclosed, for example, in US 2004/0197256 A1, U.S. Pat. Nos. 3,619,132, 4,847,062 and 6,162,263. The preparation of the alkali metal cyanides is effected by reaction of hydrogen cyanide-containing gasses with the corresponding alkalis.

Thus, US 2004/0197256 A1 relates to a process for the preparation of sodium cyanide by reacting HCN with aqueous NaOH, a solution comprising sodium cyanide being obtained, and crystallization of the sodium cyanide, a suspension of sodium cyanide crystals being obtained. The process is carried out in the presence of an acid or a metal salt of this acid, the acid having a pKa value of ≦4.8. The sodium cyanide crystals obtained are then separated from the suspension and dried. The sodium cyanide crystals obtained can be used in the cyanide process. For this purpose, the crystals are generally dissolved in water according to methods known in the prior art. The sodium cyanide crystals prepared with the aid of US 2004/0197256 A1 have a high purity. According to US 2004/0197256 A1, they are more suitable for transport to the user than sodium cyanide prepared by conventional processes and in the form of briquettes. Furthermore, the transport of the sodium cyanide crystals prepared according to this process is more economical and less environmentally hazardous in the transport of aqueous sodium cyanide solutions.

U.S. Pat. No. 3,619,132 relates to a process for the preparation of alkali metal cyanides by reaction of a hydrogen cyanide-comprising carbon dioxide-free crude gas with aqueous alkali metal hydroxide in a first step at a pressure below atmospheric pressure, the alkali metal cyanide being formed, and subsequent crystallization of the alkali metal cyanide in a second step at a pressure below the pressure in the first step.

Sodium cyanide crystals are obtained, which are subsequently dried, sodium cyanide being obtained in high purity.

U.S. Pat. No. 4,847,062 relates to a process for the preparation of sodium cyanide crystals by reaction of hydrogen cyanide-comprising crude gas which is prepared by means of the Andrussow process, comprising oxides of carbon and water, with sodium hydroxide. Sodium cyanide is isolated in the form of crystals from the aqueous sodium cyanide solution obtained. The sodium cyanide crystals obtained are generally shaped into briquettes and transported to the user, who then once again dissolves the sodium cyanide in water and uses the aqueous solution, for example, for extracting metals from metal-containing ores.

U.S. Pat. No. 6,162,263 relates to a process for the preparation of metal cyanides which are suitable for transport. The metal cyanides are obtained in the form of a moist "cake".

The known processes for the preparation of cyanides assume that the cyanide will be produced by a producer outside the range of an ore mine in which the cyanide process is effected. The cyanide is then transported as a solid or, if appropriate, as concentrated solution. In the mine, the cyanide is then diluted to the concentration necessary for the cyanide process. The use of wastewater, which occurs as depleted wastewater in the cyanide process, for the preparation of cyanide solutions is not described in the prior art.

An object of the present invention is therefore the provision of metal cyanide-comprising aqueous solutions, at least a part of the water being obtained from wastewater which occurs in the cyanide process. As a result, the amount of wastewater formed in the cyanide process can be reduced and the costs for disposal of the cyanide-containing wastewater can be cut.

The achievement of the object starts from solutions comprising water and at least one metal cyanide.

In this case, in the solution according to the invention, at least a part of the water is obtained from wastewater which occurs as depleted wastewater in a process for the extraction of noble metals from noble metal-containing ores by the cyanide process.

The depleted wastewater obtained in the cyanide process usually comprises solids and/or heavy metals, for example zinc. These solids are preferably separated off before the use of the wastewater in the solutions according to the invention, so that wastewater which is a depleted wastewater clarified to remove solids and/or heavy metals and occurring in the cyanide process is preferably used in the solutions according to the invention. The separation of the solids and/or heavy metals from the depleted wastewater occurring in the cyanide process is effected in general by methods known to the person skilled in the art.

The solutions according to the invention optionally comprise, in addition to the part of the water which is obtained from the abovementioned wastewater, a further proportion of water which is formed by fresh water. This fresh water may be water which has not been particularly purified, e.g. tap water or river water, or purified water, for example demineralized water.

In general, the proportion of the water obtained from the wastewater is from 0.1 to 100% by weight, preferably from 5 to 95% by weight, particularly preferably from 10 to 90% by weight. The proportion of fresh water, based on the water used in the solutions according to the invention, is in general from 0 to 99.9% by weight, preferably from 5 to 95% by weight, particularly preferably from 10 to 90% by weight. In a preferred embodiment, a part of the water is therefore fresh water and a part of the water is obtained from wastewater.

Processes for extracting noble metals from noble metal-containing ores by the cyanide process are known to the person skilled in the art. A description of the entire cyanide process and in particular the treatment of the wastewater is disclosed, for example, in: Technical Report "Treatment of Cyanide Heap Leaches and Tailings", September 1994, U.S. Environmental Protection Agency, Office of Solid Waste, Special Waste Branch, 401 M Street, SW, Washington, DC 20460.

In general, the cyanide process is used for extracting silver or gold, in particular for extracting gold. Various leaching processes are known in the prior art. Thus, the leaching can be effected as so-called heap leaching, stir-leaching or percolation in tanks (tank leaching). According to the present invention, a depleted wastewater which is obtained in heap leaching is used. Suitable processes for heap leaching are known to the person skilled in the art.

Metal cyanides used in the solutions according to the invention are preferably alkali metal or alkaline earth metal cyanides, particularly preferably Li, Na, K or Ca cyanide, very particularly preferably Na cyanide or Ca cyanide.

The metal cyanide is present in the solutions according to the invention preferably in an amount of from 0.001 to 35% by weight, preferably from 0.01 to 30% by weight, very particularly preferably from 0.02 to 10% by weight, based on the total weight of the solutions. These solutions can—depending on the concentration of metal cyanide—be used directly in the cyanide process, preferably in so-called heap leaching, or can be further diluted before use in the cyanide process. Conventional concentrations of metal cyanide of the solutions suitable for the cyanide process are known to the person skilled in the art. Suitable concentrations in which metal cyanide is used are, for example, from 10 to 1000 ppm, preferably from 50 to 500 ppm.

The solutions according to the invention are usually alkaline solutions. The solutions according to the invention preferably have a pH of from 7 to 13.5, particularly preferably from 8 to 13, very particularly preferably from 9 to 12.5. The pH can be adjusted with all customary basic materials. NaOH, CaO, $Ca(OH)_2$ or mixtures of said substances, such as, for example, lime or slaked lime, are particularly suitable.

The solutions according to the invention can be prepared by processes known to the person skilled in the art, a part of the water used being obtained from wastewater which occurs as depleted wastewater in a process for extracting noble metals from noble metal-containing ores by the cyanide process.

The present invention therefore furthermore relates to a process for the preparation of the solutions according to the invention, comprising:

(i) reaction of hydrogen cyanide or hydrogen cyanide-containing gasses with a solution comprising at least one metal hydroxide and/or metal oxide and/or mixed oxide and water;

(ii) if appropriate, dilution of the solution obtained in step (i) with water;

in at least one of the steps (i) and (ii) at least a part of the water being obtained from wastewater which occurs as depleted wastewater in a process for extracting noble metals from noble metal-containing ores by the cyanide process.

The wastewater used is preferably depleted wastewater clarified to remove solids and/or heavy metals and occurring in the cyanide process, as already mentioned above. Suitable cyanide processes in which the wastewater occurs have also already been mentioned above.

Step (i)

The hydrogen cyanide used in step (i) or the hydrogen cyanide-containing gases used in step (i) can be prepared by any desired processes known to the person skilled in the art. Suitable processes for the industrial production of hydrogen cyanide are, for example, the reaction of hydrocarbons, in particular methane, with ammonia (Andrussow process, BMA process). Both in the Andrussow process and in the BMA process, the use of a noble metal catalyst is required.

A further possibility for the preparation of hydrogen cyanide is the dehydration of formamide. In general, methanol and methyl formate are first prepared from synthesis gas ($CO/H_2$), the methyl formate then being transamidated with ammonia to give formamide. The formamide is thermally labile and decomposes at high temperatures to give hydrogen cyanide and water. The cleavage is very selective. In this way, it is possible to obtain a cleavage gas which has a high concentration of hydrogen cyanide and only small amounts of ammonia or other gaseous substances, such as $CO_2$, CO or $H_2$. Furthermore, no expensive noble metal catalyst is required in the process for the preparation of hydrogen cyanide by dehydration of formamide, and the process does not require complicated apparatuses. Suitable processes for the preparation of hydrogen cyanide by dehydration of formamide are mentioned, for example, in EP-A 0 209 039, DE-A 101 385 53 and WO 2004/050587.

The preparation of a hydrogen cyanide or of hydrogen cyanide-comprising gases in step (i) of the process according to the invention is preferably effected by dehydration of formamide, in particular by one of the abovementioned processes, since the high-boiling formamide can be easily and safely transported and can be used in a simple and economical thermolysis plant in the area of a noble metal mine for the preparation of HCN. Particularly preferably, hydrogen cyanide is prepared by catalytic dehydration of gaseous formamide in a reactor which has an inner reactor surface of steel comprising iron and chromium and nickel, the reactor very particularly preferably being a tubular reactor which comprises no further internals. A suitable reactor and a suitable process are disclosed, for example, in WO 2004/050587.

For reaction with a solution comprising at least one metal hydroxide and/or metal oxide and/or mixed oxide and water, the hydrogen cyanide being used in gaseous form, in particular as a gaseous mixture comprising hydrogen cyanide, or in liquid form. Suitable processes for the preparation of metal cyanides by reacting hydrogen cyanide with a solution comprising at least one metal hydroxide and/or metal oxide and/or mixed oxide and water are known to the person skilled in the art and have already been mentioned above.

In a preferred embodiment, the reaction in step (i) is effected by reaction of a hydrogen cyanide-comprising crude gas which is particularly preferably obtained by dehydration of formamide with the solution comprising at least one metal hydroxide and/or metal oxide and/or mixed oxide and water. The hydrogen cyanide-comprising crude gas can be freed by acid scrubbing from ammonia formed in small amounts as a byproduct in the hydrogen cyanide preparation before the reaction with the solution comprising at least one metal hydroxide and/or metal oxide and/or mixed oxide and water. The acid used thereby may be any mineral acid, sulfuric or phosphoric acid being preferred. If the hydrogen cyanide is prepared by dehydration of formamide, which is preferred, acid scrubbing is generally unnecessary since only very small amounts of ammonia form as a byproduct in the preparation of hydrogen cyanide. Suitable acid scrubbing methods are disclosed, for example in Ullmann's Encyclopedia of Industrial Chemistry, 6th Edition, Chapter on HCN.

In general, step (i) of the process according to the invention is carried out so that a crude gas treated, if appropriate, with acid and comprising hydrogen cyanide is passed into an aqueous solution which comprises at least one metal hydroxide and/or metal oxide and/or mixed oxide.

Preferably used metal hydroxides and/or metal oxides and/or mixed oxides are alkali metal and alkaline earth metal hydroxides and/or alkaline earth metal hydroxides and/or alkaline earth metal oxides and/or alkaline earth metal mixed oxides, particularly preferably Li, Na, K or Ca hydroxide and/or Ca oxide and/or Ca mixed oxide, very particularly preferably Na hydroxide or Ca hydroxide and/or Ca oxide and/or mixed oxide. The Ca hydroxide and/or Ca oxide and/or Ca mixed oxide may be, for example, unslaked lime or slaked lime, CaO, $Ca(OH)_2$. Depending on the metal hydroxide and/or metal oxide and/or mixed oxide used, the corresponding metal cyanide is formed. In the case of a very particularly preferred use of Na hydroxide or Ca hydroxide and/or Ca oxide and/or Ca mixed oxide, Na cyanide or Ca cyanide is thus obtained.

In general, the solution comprising at least one metal hydroxide and water comprises from 5 to 50% by weight, preferably from 15 to 50% by weight, particularly preferably from 30 to 50% by weight, of the metal hydroxide and/or metal oxide and/or mixed oxide used.

The reaction temperature in step (i) is in general from 5 to 100° C., preferably from 10 to 80° C., particularly preferably from 20 to 60° C.

Usually, hydrogen cyanide-comprising gas is passed into the solution comprising at least one metal hydroxide and/or metal oxide and/or mixed oxide and water until an excess of hydroxide and/or oxide and/or mixed oxide of in general from 0.1 to 5% by weight, preferably from 0.2 to 2.0% by weight, is reached. When said excess of hydroxide and/or oxide and/or mixed oxide is reached, the introduction of the hydrogen cyanide-comprising gas is stopped.

The solution of the desired cyanide salt in water is obtained. The content of cyanide salts in solution is dependent on the amount of hydroxide and/or oxide and/or mixed oxide used in the solution.

In general, a solution which has a content of desired cyanide salt of from 0.001 to 35% by weight, preferably from 0.01 to 30% by weight, particularly preferably from 0.02 to 10% by weight, is obtained.

A preferred process for the preparation of solutions comprising water and at least one metal cyanide is disclosed, for example, in the prior unpublished application of Jun. 7, 2005 with the application number DE 10 2005 026 326.7 and the title "Process for the preparation of cyanide salts".

The solution obtained in step (i) and comprising at least one metal cyanide and water can be diluted in a further step to the desired concentration of use of in general from 10 to 1000 ppm, preferably from 50 to 500 ppm, if the solution obtained in step (i) comprises the metal cyanide in higher concentration.

Step (ii)

In step (ii), which is optional, dilution of the solution obtained in step (i) of the process according to the invention is effected with water. Ready-to-use solutions comprising water and at least one metal cyanide, which can be used directly in the cyanide process, are obtained thereby.

In principle, it is possible to carry out the entire process according to the invention, comprising step (i) and step (ii), in the ore mine. However, it is also conceivable to carry out step (i) of the process according to the invention at a location other than that of the ore mine and to carry out only the dilution in step (ii) at the location of the ore mine.

In a further embodiment, it is possible to carry out only step (i), a ready-to-use solution having the abovementioned concentrations of the at least one metal cyanide being obtained directly. Dilution according to step (ii) can be dispensed with in this case.

According to the invention, in at least one of the steps (i) and (ii), at least a part of the water is obtained from wastewater which occurs as depleted wastewater in a process for the extraction of noble metals from noble metal-containing ores by the cyanide process. It is possible for the wastewater to be used for the preparation of the solution used in step (i) and comprising at least one metal hydroxide and/or metal oxide and/or mixed oxide and water. The wastewater can even be used for dissolving the metal hydroxide or only for diluting the solution comprising at least one metal hydroxide and/or metal oxide and/or mixed oxide and water to the desired concentration of metal hydroxide and/or metal oxide and/or mixed oxide. Furthermore, it is possible for the wastewater to be used in step (ii) for diluting the solution obtained in step (i) and comprising at least one metal cyanide and water to the desired concentration of use, if step (ii) is carried out. It is also possible to use wastewater both in step (i) and in step (ii). If step (ii) is not carried out, the wastewater is used in step (i). In a preferred embodiment of the process according to the invention, a part of the water required for the preparation of the solutions according to the invention, comprising water and at least one metal cyanide, is formed by fresh water. This is advantageous for avoiding, if appropriate, possible increases in the concentration of foreign substances which may arise as a result of the depleted water occurring in the cyanide process being circulated. Usually, the preferred addition of fresh water is effected in a form such that a purge stream of the depleted wastewater occurring in the cyanide process is continuously replaced with fresh water.

Suitable proportions of fresh water and wastewater in the solutions according to the invention have already been mentioned above.

The solutions according to the invention or the solutions prepared by the process according to the invention and comprising water and at least one metal cyanide are preferably used in a process for extracting the noble metals from noble metal-containing ores by the cyanide process.

The present invention furthermore relates to a process for extracting noble metals from noble metal-containing ores by the cyanide process, wherein the solution according to the invention is used, and to the use of the solution according to the invention in a process for extracting noble metals from noble metal-containing ores by the cyanide process. Suitable processes for extracting noble metals by the cyanide process are known to the person skilled in the art and have already been mentioned above. Preferably, the process for extracting silver or gold, particularly preferably gold, from the corresponding ores is used. The cyanide process is preferably effected by heap leaching, the heap leaching being disclosed in the prior art.

The present invention furthermore relates to the use of depleted wastewater occurring in the extraction of noble metals from noble metal-containing ores by the cyanide process for the preparation of solutions comprising water and at least one metal cyanide.

The depleted wastewater is preferably clarified by methods known to the person skilled in the art to remove solids and/or heavy metals before use for the preparation of solutions comprising water and at least one metal cyanide. Suitable metal cyanides in suitable amounts of metal cyanide are mentioned above. The prepared solutions comprising water and at least one metal cyanide comprise fresh water and wastewater. Preferred proportions of fresh water and wastewater in the solutions comprising water and at least one metal cyanide are likewise mentioned above.

The following examples additionally explain the invention.

EXAMPLES

Preparation of a Crude Gas Comprising Hydrogen Cyanide

A 4.5 m long reaction tube of 1.4541 steel (V2A steel) having an internal diameter of 10 mm and an external diameter of 12 mm is brought electrically to a constant external temperature of 520° C. The reaction tube has a specific surface area of 400 $m^2/m^3$. The internal pressure in the tube is 100 mbar abs and is produced by a vacuum pump.

In an upstream evaporator, which is likewise under the reaction pressure, 1.3 kg/h of formamide are vaporized at 145° C. and passed to the top of the reaction tube. In addition, 13 1 (STP) of air/h are fed in at the connection between evaporator and reaction tube.

At the end the reaction tube, the sample is taken and is analyzed for its constituents. The analysis gave a formamide conversion of 98.5% and a hydrogen cyanide selectivity, based on formamide, of 93.2%.

1 Preparation of Cyanide Salt Solutions (Comparison)

The procedure for the preparation of hydrogen cyanide-comprising crude gas: example A1 (formamide conversion: 98.5%; hydrogen cyanide selectivity: 93.2%).

The composition of the crude gas obtained in example A1 is as follows (in % by weight): 55.5% of HCN; 38.0% of water; 1.5% of formamide; 1.7% of $NH_3$; 2.9% of $CO_2$; 0.2% of $H_2$; 0.2% of CO.

For removal of $NH_3$, the crude gas is passed through a cooled (20° C.) concentrated sulfuric acid. The crude gas obtained in this manner comprises no detectable $NH_3$.

The neutralization effected by passing the HCN-comprising crude gas (temperature of the crude gas: 100° C.) into 25 l stirred container in which about 10 l of a 40% strength by weight aqueous NaOH solution are initially taken. 30 l of demineralized water are added to this for further dilution. During the neutralization at 40° C. (external cooling), the content of free NaOH is constantly monitored (sampling). At an excess of about 1.5% of NaOH, the introduction of gas is stopped. A cyanide content of 50 ppm by weight is then established with additional demineralized water.

2 Preparation of Cyanide Salt Solution (According to the Invention)

The procedure for the preparation of hydrogen cyanide-comprising crude gas: example A1 (formamide conversion: 98.5%; hydrogen cyanide selectivity: 93.2%).

The composition of the crude gas obtained in example A1 is as follows (in % by weight): 55.5% of HCN; 38.0% of water; 1.5% of formamide; 1.7% of $NH_3$; 2.9% of $CO_2$; 0.2% of $H_2$; 0.2% of CO.

For removal of $NH_3$, the crude gas is passed through a cooled (20° C.) concentrated sulfuric acid. The crude gas obtained in this manner comprises no detectable $NH_3$.

The neutralization is effected by passing the HCN-comprising crude gas (temperature of the crude gas: 100° C.) into a 25 l stirred container in which about 10 l of a 40% strength by weight aqueous NaOH solution are initially taken. According to the invention, 30 l of cyanide-containing wastewater (content=31 ppm by weight) from the process for leaching gold ore (heap leaching) are added to this for further dilution. During the neutralization at 40° C. (external cooling), the content of free NaOH is constantly monitored (sampling). At an excess of about 1.5% of NaOH, the introduction of gas is stopped. The cyanide content of 50 ppm by weight is then established with cyanide-containing wastewater.

Column Experiments:

Column experiments in which representative samples of the gold-containing rock are packed in columns and leached with alkaline cyanide solutions serve as a model of the heap leaching carried out industrially.

The leaching is effected in each case over 30 days at a flow rate of 180 ml per day per kg of ore.

The columns have an internal diameter of 12 cm, and a length of 120 cm and are filled in each case with 25 kg of ore. The ore is milled to a particle size x of $0.5 \leq x \leq 2.5$ cm and is sieved. The gold content is in each case 0.5-1.5 g/t of rock. Ores from the Minera Yanacocha (experiment numbers 1a and 2a) and Minera Nueva Calif. (experiment numbers 1b and 2b) mines, Carretea Mancos km 15, Distrito de Mancos, Provincia Yungay, Ancash, Peru, are used. The results are summarized in table 1.

The cumulative % data for the gold yield relate to the total gold content of the individual columns. The gold content is determined by means of ICP-OES (Inductively Coupled Plasma-Optical Emission Spectroscopy) on a Vista MPX from Varian, Inc., Darmstadt.

TABLE 1

| Expt. No. | Diluent | Cyanide concentration (ppm by weight) | Au yield (%) | Wastewater (liters) after active carbon | Gold ore |
|---|---|---|---|---|---|
| 1a | Demineralized water | 50 | 79 | 4.9 | Yanacocha |
| 1b | Demineralized water | 50 | 78 | 4.9 | Nueva C |
| 2a | Cyanide wastewater | 50 | 79 | 0.6*) | Yanacocha |
| 2b | Cyanide wastewater | 50 | 81 | 0.6*) | Nueva C |

*)The wastewater is obtained as follows. The outflow of the column leaching is collected over 30 days (5.2 l) and the dissolved gold-containing complex is separated by means of an active carbon filter from the remaining liquid by absorption. The outflow of the active carbon filtration (4.9 l) still comprises about 30 ppm of sodium cyanide. This wastewater is used for the preparation of NaCN solution. A part-stream (0.6 l) is replaced by fresh demineralized water in order to avoid increases in concentrations due to heavy metals, etc.

We claim:

1. A process for the preparation of solutions comprising water and at least one metal cyanide comprising:

(i) reacting hydrogen cyanide or hydrogen cyanide-containing gasses with a solution comprising at least one metal hydroxide and/or metal oxide and/or mixed oxide and water; and (ii) diluting the solution obtained in step (i) with water;

wherein in step (i) at least a part of the water is obtained from wastewater which occurs as depleted wastewater in a process for extracting noble metals from noble metal-containing ores by the cyanide process.

2. The process according to claim 1, wherein the wastewater used is depleted wastewater clarified to remove solids and/or heavy metals and occurring in the cyanide process.

3. The process according to claim 1, wherein the at least one metal hydroxide and/or metal oxide and/or mixed oxide is an alkali metal or alkaline earth metal hydroxide and/or an alkaline earth metal oxide and/or an alkaline earth metal mixed oxide.

4. The process according to claim 3, wherein the at least one alkali metal or alkaline earth metal hydroxide and/or alkaline earth metal oxide and/or alkaline earth metal mixed oxide is Li, Na, K or Ca hydroxide and/or Ca oxide and/or Ca mixed oxide.

5. The process according to claim 4, wherein the at least one Li, Na, K or Ca hydroxide and/or Ca oxide and/or Ca mixed oxide is Na hydroxide or Ca hydroxide and/or Ca oxide and/or Ca mixed oxide.

6. The process according to claim 1, wherein in step (i) at least a part of the water is fresh water.

7. The process according to claim 6, wherein the fresh water is selected from the group consisting of tap water, river water and demineralized water.

8. The process according to claim 1, wherein in step (i) a reaction temperature is in a range of from 5 to 100° C.

9. The process according to claim 1, wherein step (i) and step (ii) are carried out in an ore mine.

10. The process according to claim 6, wherein the water obtained from wastewater is 10 to 90% by weight, based on the total amount of water in step (i).

* * * * *